United States Patent [19]  
Takahashi et al.

[11] Patent Number: 4,686,232  
[45] Date of Patent: Aug. 11, 1987

[54] FUNGICIDAL ANILINE DERIVATIVES

[75] Inventors: Junya Takahashi, Hyogo; Mitsuru Sasaki; Hiroshi Noguchi, both of Osaka; Toshiro Kato, Hyogo, all of Japan

[73] Assignee: Sumitomo Chemical Company, Limited, Osaka, Japan

[21] Appl. No.: 577,352

[22] Filed: Feb. 6, 1984

[30] Foreign Application Priority Data

Feb. 28, 1983 [GB] United Kingdom ............... 8305485  
Jun. 3, 1983 [GB] United Kingdom ............... 8315314

[51] Int. Cl.⁴ ............... A01N 37/18; A01N 43/02; C07D 319/08
[52] U.S. Cl. ............... 514/365; 549/365; 549/362; 549/439; 549/350; 549/351; 514/466; 514/452; 514/412; 514/398; 514/397; 514/392; 514/376; 564/180; 564/155; 564/74
[58] Field of Search ............... 549/362, 365, 439, 350, 549/351; 514/397, 398, 365, 392, 376, 412, 452, 466; 260/455 A; 564/74, 155, 180

[56] References Cited

U.S. PATENT DOCUMENTS

| 2,530,831 | 11/1950 | Lott ............... 549/362 |
| 3,334,126 | 8/1967 | Miyazaki et al. ............... 260/455 A |
| 3,636,032 | 1/1972 | Breuer ............... 260/455 A |
| 3,808,191 | 4/1974 | Poduska et al. ............... 260/455 A |
| 4,460,603 | 7/1984 | Chan ............... 564/74 |

FOREIGN PATENT DOCUMENTS 0465967 6/1950 Canada ............... 549/365  
0051871 5/1982 European Pat. Off.  
0103173 3/1984 European Pat. Off. ............ 549/365  
7110526 3/1971 Japan ............... 564/155  
5549350 4/1980 Japan ............... 564/74  
0216184 12/1983 Japan ............... 549/365  
0013782 1/1985 Japan ............... 549/365  
2109368 6/1983 United Kingdom ............... 549/362

OTHER PUBLICATIONS

Heertjes et al., Journ. Chem. Society, pp. 3445–3447 (1957).

Primary Examiner—Nicky Chan  
Attorney, Agent, or Firm—Birch, Stewart, Kolasch & Birch

[57] ABSTRACT

A compound of the formula:

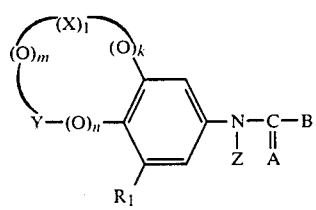

useful as a fungicidal agent against phytopathogenic fungi, particularly strains thereof which are resistant to benzimidazole or thiophanate fungicides and/or cyclic imide fungicides.

24 Claims, No Drawings

FUNGICIDAL ANILINE DERIVATIVES

This invention relates to fungicidal aniline derivatives.

Benzimidazole and thiophanate fungicides such as Benomyl(methyl 1-(butylcarbamoyl)benzimidazol-2-ylcarbamate), Fubelidazol(2-(2-furyl)benzimidazole), Thiabendazole(2-(4-thiazolyl)benzimidazole), Carbendazim(methyl benzimidazol-2-ylcarbamate), Thiophanate-methyl(1,2-bis(3-methoxycarbonyl-2-thioureido)-benzene), Thiophanate(1,2-bis(3-ethoxycarbonyl-2-thioureido)benzene), 2-(O,S-dimethylphosphorylamino)-1-(3'-methoxycarbonyl-2'-thioureido)benzene and 2-(O,O-dimethylthiophosphorylamino)-1-(3'-methoxycarbonyl-2'-thioureido)benzene are known to show an excellent fungicidal activity against various plant pathogenic fungi, and they have been widely used as agricultural fungicides since 1970. However, their continuous application over a long period of time provides phytopathogenic fungi with tolerance to them, whereby their plant disease-preventive effect is much lowered. Further, the fungi which gained tolerance to certain kinds of benzimidazole or thiophanate fungicides also show considerable tolerance to some other kinds of benzimidazole or thiophanate fungicides. Thus, they are apt to obtain cross-tolerance. Therefore, if any material decrease of their plant disease-preventive effect in certain fields is observed, their application to such fields has to be discontinued. But, it is often observed that the density of drug-resistant organisms is not decreased even long after the application has been discontinued. Although other kinds of fungicides have to be employed in such case, only a few are as effective as benzimidazole or thiophanate fungicides in controlling various phytopathogenic fungi. Benzimidazole and thiophanate fungicides will be hereinafter referred to as "benzimidazole thiophanate fungicides".

Cyclic imide fungicides such as Procymidone (3-(3',5'-dichlorophenyl)-1,2-dimethylcyclopropane-1,2-dicarboximide), Iprodione(3-(3',5'-dichlorophenyl)-1-isopropylcarbamoylimidazolidine-2,4-dione), Vinchlozolin(3-(3',5'-(dichlorophenyl)-5-methyl-5-vinyloxazolidin-2,4-dione), ethyl(RS)-3-(3',5'-dichlorophenyl)-5-methyl-2,4-dioxooxazolidine-5-carboxylate, etc., which are effective against various plant diseases, particularly those caused by *Botrytis cinerea*, have the same defects as previously explained with respect to the benzimidazole thiophanate fungicides.

In C.R. Acad. Sc. Paris, t. 289, Serie D, pages 691–693 (1979), it is described that such herbicides as Barban(4-chloro-2-butynyl N-(3-chlorophenyl)carbamate), Chlorobufam(1-methyl-2-propynyl N-(3-chlorophenyl)carbamate), Chlorpropham(isopropyl N-(3-chlorophenyl)carbamate) and Propham (isopropyl N-phenylcarbamate) exhibit a fungicidal activity against certain organisms tolerant to some of the benzimidazole thiophanate fungicides. However, their fungicidal activity against the drug-resistant fungi is not strong enough, and hence, practically they can not be used as fungicides.

As a result of a study seeking a new type of fungicides, it has now been found that compounds of the formula:

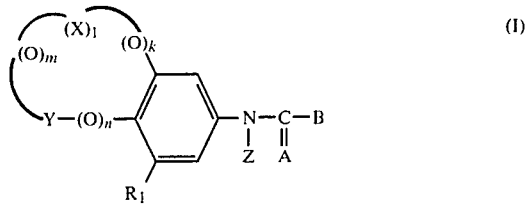

wherein X and Y are, the same or different, a lower alkylene group or a lower alkoxy(lower)alkylene group; k, l, m and n are, the same or different, 0 or 1; $R_1$ is a lower alkyl group, a lower alkoxy group, a lower alkoxymethyl group, a lower alkoxycarbonyl group, a hydrogen atom, a halogen atom, an acyl group or a cyano group; Z is a hydrogen atom, a lower alkyl group, a lower alkenyl group, a lower alkynyl group, a lower alkoxycarbonyl(lower)alkyl group or a group of the formula:

or $-S-R_3$ in which $R_2$ is a lower alkyl group, a cyclo(lower)alkyl group or a phenyl group and $R_3$ is a lower alkyl group, a phenyl group or a lower alkoxycarbonyl group; A is an oxygen atom or a sulfur atom; and B is a lower alkyl group, a lower alkenyl group, a cyclo(lower)alkyl group, a phenyl group or a group of the formula: $-W-R_4$ in which W is an oxygen atom or a sulfur atom and $R_4$ is a lower alkyl group, a lower alkenyl group, a lower alkynyl group, a halo(lower)alkenyl group, a halo(lower)alkynyl group, a cyclo(lower)alkyl group, a phenyl group optionally substituted with halogen or a lower alkyl group substituted with at least one member selected from the group consisting of halogen, cyano, phenyl, cyclo(lower)alkyl or lower alkoxy, show an excellent fungicidal activity against plant pathogenic fungi which have developed resistance to benzimidazole and thiophanate fungicides and/or cyclic imide fungicides. It is notable that their fungicidal potency against the organisms tolerant to benzimidazole and thiophanate fungicides and/or cyclic imide fungicides (hereinafter referred to as "drug-resistant fungi" or "drug-resistant strains") is much higher than that against the organisms sensitive to benzimidazole and thiophanate fungicides and/or cyclic imide fungicides (hereinafter referred to as "drug-sensitive fungi" or "drug-sensitive strains").

The term "lower" used hereinabove and hereinafter in connection with organic radicals or compounds indicates that such radicals or compounds each have not more than 6 carbon atoms.

The compounds of the formula (I) are fungicidally effective against a wide scope of plant pathogenic fungi, of which examples are as follows: *Podosphaera leucotricha*, *Venturia inaequalis*, *Mycosphaerella pomi*, *Marssonina mali* and *Sclerotinia mali* of apple, *Phyllactinia kakicola* and *Gloeosporium kaki* or persimmon, *Cladosporium carpophilum* and *Phomopsis sp.* of peach, *Cercospora viticola*, *Uncinula necator*, *Elsinoe ampelina* and *Glomerella cingulata* of grape, *Cercospora beticola* of sugarbeet, *Cercospora arachidicola* and *Cercospora personata* of peanut, *Erysiphe graminis* f. sp. hordei, *Cercosporella herpotrichoides* and *Fusarium nivale* of barley, *Erysiphe graminis* f. sp. tritici of wheat, *Sphaerotheca*

*fuliginea* and *Cladosporium cucumerinum* of cucumber, *Cladosporium fulvum* of tomato, *Corynespora melongenae* of eggplant, *Sphaerotheca humuli*, *Fusarium oxysporum* f. sp. *fragariae* of strawberry, *Botrytis alli* of onion, *Cercospora apii* of celery, *Phaeoisariopsis griseola* of kidney bean, *Erysiphe cichoracearum* of tobacco, *Diplocarpon rosae* of rose, *Elsinoe fawcetti, Penicillium italicum, Penicillium digitatum* of orange, *Botrytis cinerea* of cucumber, eggplant, tomato, strawberry, pimiento, onion, lettuce, grape, orange, cyclamen, rose or hop, *Sclerotinia sclerotiorum* of cucumber, eggplant, pimiento, lettuce, celery, kidney bean, soybean, azuki bean, potato or sunflower, *Sclerotinia cinerea* of peach or cherry, *Mycosphaerella melonis* of cucumber or melon, etc. Namely, the compounds of the formula (I) are highly effective in controlling the drug-resistant strains of said fungi.

The compounds of the formula (I) are also fungicidally effective against fungi sensitive to said known fungicides as well as fungi to which said known fungicides are ineffective. Examples of such fungi are *Pyricularia oryzae, Pseudoperonospora cubensis,* Plasmopara, viticola, *Phytophthora infestans,* etc.

Advantageously, the compounds of the formula (I) are of low toxicity and have little detrimental actions on mannals, fishes and so on. Also, they may be applied to the agricultural field without causing any material toxicity to important crop plants.

The compounds (I) can be prepared by either one of the following procedures:

Procedure (a):

The compound (I) can be prepared by reacting a compound of the formula:

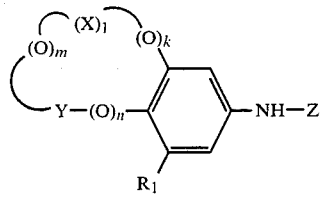

(II)

wherein $R_1$, X, Y, k, l, m, n and Z are each as defined above with a compound of the formula:

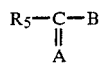

(III)

wherein A and B are each as defined above and $R_5$ is a halogen atom.

The reaction is usually carried out in an inert solvent (e.g. water, benzene, toluene, xylene, diethyl ether, tetrahydrofuran, dioxane, chloroform, carbon tetrachloride, ethyl acetate, pyridine, N,N-dimethylformamide). The reaction may be performed in the presence of a base (e.g. pyridine, triethylamine, N,N-diethylaniline, sodium hydride, potassium hydroxide). If desired, a phase transfer catalyst (e.g. tetra-n-butylammonium bromide) can be used so as to obtain the compound (I) in a high yield. The reaction may be accomplished at a temperature of 0° to 150° C. within 10 hours.

The compound (II) wherein Z is hydrogen is prepared by reducing a compound of the formula:

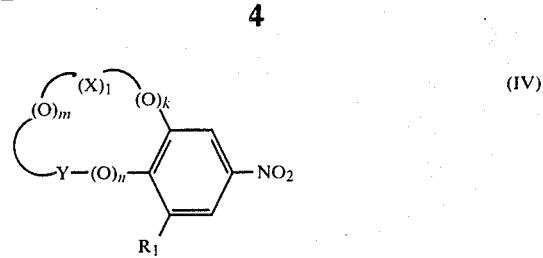

(IV)

wherein X, Y, k, l, m, n and $R_1$ are each as defined above.

The reduction may be performed in an inert solvent (e.g. water, methanol, ethanol or their mixture) with a reducing agent (e.g. sodium sulfide, sodium hydrosulfide) at a temperature of 50° C. to the boiling point of the solvent within 12 hours.

The reduction may be also performed in an aqueous organic or inorganic acid (e.g. acetic acid, hydrochloric acid, sulfuric acid) with metal dust (e.g. iron dust, zinc dust, tin dust) at a temperature of 50° to 100° C. within 12 hours.

The reduction may be also accomplished by catalytic hydrogenation, for instance, treatment with a catalyst (e.g. platinum oxide, palladium-carbon) in an organic solvent (e.g. ethanol, ethyl acetate) under an ordinary or elevated pressure at a temperature of 0° to 60° C.

The compound (IV) is obtainable by a known method [cf. J. Chem. Soc., 1933, 699].

The compound (II) wherein Z is other than hydrogen may be prepared by reacting a compound of the formula:

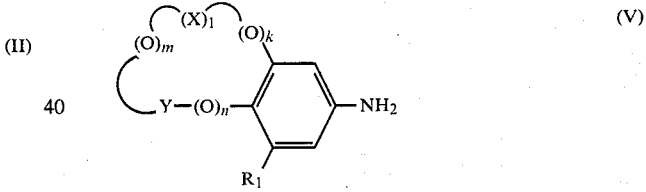

(V)

wherein $R_1$, X, Y, k, l, m and n are each as defined above, with a compound of the formula:

Z—$R_7$     (VI)

wherein Z is as defined above and $R_7$ is a leaving group (e.g. a halogen atom, a tosyloxy group, a mesyloxy group).

The reaction may be performed in a solvent (e.g. water, N,N-dimethylformamide, dimethylsulfoxide, tetrahydrofuran, dioxane, toluene, benzene, diethyl ether or their mixture) with a base (e.g. sodium hydroxide, potassium carbonate, sodium hydride, N,N-diethylaniline, pyridine). If desired, a phase transfer catalyst (e.g. tetra-n-butylammonium bromide) may be used. The reaction proceeds at a temperature 0° to 100° C. within 12 hours.

Procedure (b):

The compound (I) wherein Z is hydrogen and B is a group of the formula: W—$R_4$ in which W and $R_4$ are each as defined above can be prepared by reacting a compound of the formula:

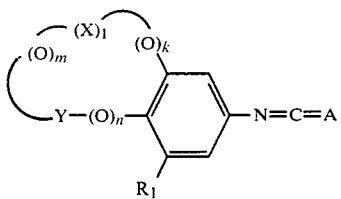

wherein X, Y, k, l, m, n, A and R₁ are each as defined above with a compound of the formula:

R₄—W—H (VIII)

wherein R₄ and W are each as defined above.

The reaction is usually carried out in the absence or presence of an inert solvent (e.g. benzene, toluene, xylene, diethyl ether, tetrahydrofuran, dioxane, N,N-dimethylformamide, chloroform, carbon tetrachloride). When desired, a base (e.g. triethylamine, N,N-diethylaniline, 1,4-diazabicyclo[2.2.2]octane) may be used as a catalyst. The reaction normally proceeds at a temperature of 0° to 50° C. within 10 hours.

The compound (VII) is obtainable by reacting the compound (V) with phosgene or thiophosgene. The reaction may be performed in an organic solvent (e.g. benzene, toluene, xylene, ethyl acetate) at a temperature of 50° C. to the boiling point of the solvent within 10 hours.

Procedure (c):

The compound (I) wherein Z is other than hydrogen may be prepared by reacting a compound of the formula:

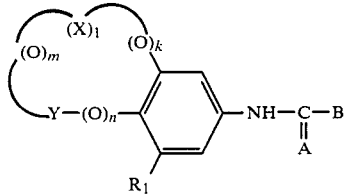

wherein R₁, X, Y, k, l, m, n, A and B are each as defined above with a compound (VI).

The reaction is performed in the presence of an organic solvent (e.g. N,N-dimethylformamide, dimethylsulfoxide, diethyl ether, tetrahydrofuran) with a base (e.g. sodium hydride, potassium hydroxide) at a temperature of 0° to 100° C. within 12 hours.

Some typical examples for preparation of the compound (I) are illustratively shown below.

Example 1 (according to Procedure (a))

6-Amino-8-chloro-1,3-benzodioxane (1.0 g) and N,N-diethylaniline (0.85 g) were dissolved in toluene (15 ml). To the resultant solution was dropwise added isopropyl chloroformate (0.70 g) in 5 minutes under ice-cooling. The resultant mixture was allowed to stand at room temperature for 12 hours, poured into ice-water and extracted with ethyl acetate. The extract was washed with water, dried over magnesium sulfate and concentrated under reduced pressure. The residue was purified by silica gel chromatography using a mixture of benzene and tetrahydrofuran as an eluent to give isopropyl N-(8-chlorobenzodioxan-6-yl)carbamate (Compound No. 33) (1.35 g) in a yield of 92.0%. M.P., 126°–128° C.

Elementary analysis: Calcd. for C₁₂H₁₄NClO₄: C, 53.05%; H, 5.16%; N, 5.16%; Cl, 13.05%. Found: C, 53.43%; H, 5.32%; N, 5.18%; Cl, 13.06%.

Example 2 (according to Procedure (b))

To a solution of 6-amino-8-ethoxy-1,3-benzodioxane (1.95 g) in toluene (20 ml), a toluene solution containing phosgene (10 g) was dropwise added at 10° to 20° C. The resultant mixture was heated gradually and, after being refluxed for 30 minutes, cooled to room temperature. The solvent was removed in vacuo, whereby crude 8-ethoxy-1,3-benzodioxan-6-ylisocyanate was obtained. This crude substance was dropwise added to a toluene solution (50 ml) containing triethylamine (1.0 g) and 2-fluoroethanol (0.70 g) at room temperature. The resultant mixture was allowed to stand at room temperature for 12 hours, poured into ice-water and extracted with ethyl acetate. The extract was washed with water, dried over magnesium sulfate and concentrated under reduced pressure. The residue was purified by silica gel chromatography using a mixture of toluene and ethyl acetate as the eluent to give 2-fluoroethyl N-(8-ethoxy-1,3-benzodioxan-6-yl)carbamate (Compound No. 10) (2.31 g) in a yield of 80.9%. M.P., 154°–154.5° C.

Example 3 (according to Procedure (c))

Sodium hydride (0.107 g; 60% dispersion in mineral oil) was dispersed in N,N-dimethylformamide (20 ml). To this solution was added isopropyl N-(8-ethoxy-1,3-benzodioxan-6-yl)carbamate (0.75 g) under ice-cooling. After being stirred at room temperature for 1 hour, phenylsulfenyl chloride (0.39 g) was added thereto under ice-cooling, and stirring was continued at room temperature overnight. The resulting mixture was poured into ice-water and extracted with ethyl acetate. The extract was washed with water, dried over magnesium sulfate and concentrated under reduced pressure. The residue was purified by silica gel chromatography using a mixture of toluene and ethyl acetate as the eluent to give isopropyl N-phenylthio-N-(8-ethoxy-1,3-benzodioxan-6-yl)carbamate (Compound 25) (0.91 g) in a yield of 87.5%. M.P., 120°–123° C.

Specific examples of the compounds (I) of the invention, which can readily be prepared according to the aforesaid procedures, are shown in Table 1.

TABLE 1

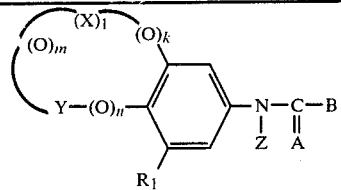

| Compound No. | X | Y | k | l | m | n | $R_1$ | A | B | Z | Physical constant |
|---|---|---|---|---|---|---|---|---|---|---|---|
| 1 | — | $CH_2$ | 1 | 0 | 0 | 1 | $C_2H_5O$ | O | $-C_2H_5$ | H | M.P. 121–122.5° C. |
| 2 | $CH_2$ | $CH_2$ | 0 | 1 | 1 | 1 | $C_2H_5O$ | O | $-CH=CHCH_3$ | H | M.P. 190–191.5° C. |
| 3 | $CH_2$ | $CH_2$ | 0 | 1 | 1 | 1 | $C_2H_5O$ | O | △ (cyclopropyl) | H | M.P. 176–179° C. |
| 4 | $CH_2$ | $CH_2$ | 0 | 1 | 1 | 1 | $C_2H_5O$ | O | —phenyl | H | M.P. 183.5–185° C. |
| 5 | $CH_2$ | $CH_2$ | 0 | 1 | 1 | 1 | $C_2H_5O$ | O | $-O(i)C_3H_7$ | H | M.P. 125–129° C. |
| 6 | $CH_2$ | $CH_2$ | 0 | 1 | 1 | 1 | $C_2H_5O$ | O | $-O-CH(CH_3)-CH=CH_2$ | H | M.P. 120.5–121.5° C. |
| 7 | $CH_2$ | $CH_2$ | 0 | 1 | 1 | 1 | $C_2H_5O$ | O | $-O-CH(CH_3)-C{\equiv}CH$ | H | M.P. 113–114° C. |
| 8 | $CH_2$ | $CH_2$ | 0 | 1 | 1 | 1 | $C_2H_5O$ | O | $-OCH_2CH=CHCH_2Cl$ | H | M.P. 95–97° C. |
| 9 | $CH_2$ | $CH_2$ | 0 | 1 | 1 | 1 | $C_2H_5O$ | O | $-OCH_2C{\equiv}CCH_2Cl$ | H | M.P. 139–141° C. |
| 10 | $CH_2$ | $CH_2$ | 0 | 1 | 1 | 1 | $C_2H_5O$ | O | $-OCH_2CH_2F$ | H | M.P. 154–154.5° C. |
| 11 | $CH_2$ | $CH_2$ | 0 | 1 | 1 | 1 | $C_2H_5O$ | O | $-OCH_2CH_2CN$ | H | M.P. 161–162° C. |
| 12 | $CH_2$ | $CH_2$ | 0 | 1 | 1 | 1 | $C_2H_5O$ | O | $-O-CH(CH_3)-$phenyl | H | M.P. 96–98° C. |
| 13 | $CH_2$ | $CH_2$ | 0 | 1 | 1 | 1 | $C_2H_5O$ | O | $-O-CH(CH_2Cl)-CH_2OCH_3$ | H | M.P. 116.5–117° C. |
| 14 | $CH_2$ | $CH_2$ | 0 | 1 | 1 | 1 | $C_2H_5O$ | O | $-O-CH(cyclopropyl)-CH_3$ | H | M.P. 126–128° C. |
| 15 | $CH_2$ | $CH_2$ | 0 | 1 | 1 | 1 | $C_2H_5O$ | O | $-O-(2\text{-F-phenyl})$ | H | M.P. 151.5–152° C. |
| 16 | $CH_2$ | $CH_2$ | 0 | 1 | 1 | 1 | $C_2H_5O$ | O | $-O-$cyclobutyl | H | M.P. 154.5–155.5° C. |
| 17 | $CH_2$ | $CH_2$ | 0 | 1 | 1 | 1 | $C_2H_5O$ | O | $-O(i)C_3H_7$ | $-CH_3$ | M.P. 88–90° C. |
| 18 | $CH_2$ | $CH_2$ | 0 | 1 | 1 | 1 | $C_2H_5O$ | O | $-O(i)C_3H_7$ | $-CH_2CH=CH_2$ | M.P. 53–54° C. |
| 19 | $CH_2$ | $CH_2$ | 0 | 1 | 1 | 1 | $C_2H_5O$ | O | $-O(i)C_3H_7$ | $-CH_2C{\equiv}CH$ | $n_D^{23.0}$ 1.5211 |
| 20 | $CH_2$ | $CH_2$ | 0 | 1 | 1 | 1 | $C_2H_5O$ | O | $-O(i)C_3H_7$ | $-CH(CH_3)-COOCH_3$ | $n_D^{23.0}$ 1.4996 |

TABLE 1-continued

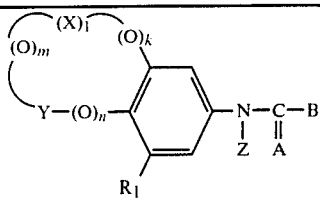

| Compound No. | X | Y | k | l | m | n | R₁ | A | B | Z | Physical constant |
|---|---|---|---|---|---|---|---|---|---|---|---|
| 21 | $CH_2$ | $CH_2$ | 0 | 1 | 1 | 1 | $C_2H_5O$ | O | $-O(i)C_3H_7$ | $-\underset{\underset{O}{\parallel}}{C}-CH_3$ | M.P. 78–81° C. |
| 22 | $CH_2$ | $CH_2$ | 0 | 1 | 1 | 1 | $C_2H_5O$ | O | $-O(i)C_3H_7$ | $-\underset{\underset{O}{\parallel}}{C}-\triangle$ | M.P. 107–110° C. |
| 23 | $CH_2$ | $CH_2$ | 0 | 1 | 1 | 1 | $C_2H_5O$ | O | $-O(i)C_3H_7$ | $-\underset{\underset{O}{\parallel}}{C}-C_6H_5$ | M.P. 105–106.5° C. |
| 24 | — | $CH_2$ | 1 | 0 | 0 | 1 | $C_2H_5O$ | O | $-O(i)C_3H_7$ | $-SCH_3$ | $n_D^{25.0}$ 1.5422 |
| 25 | $CH_2$ | $CH_2$ | 0 | 1 | 1 | 1 | $C_2H_5O$ | O | $-O(i)C_3H_7$ | $-S-C_6H_5$ | M.P. 120–123° C. |
| 26 | — | $CH_2$ | 1 | 0 | 0 | 1 | $C_2H_5O$ | O | $-O(i)C_3H_7$ | $-SCOOC_2H_5$ | NMR δ ($CDCl_3$): 6.39(s,2H), 5.82 (s,2H), 4.86(m,1H), 4.22(q,2H), 4.02 (q,2H), 1.22(d,6H), 1.20–1.65(m,6H). |
| 27 | $CH_2$ | $CH_2$ | 0 | 1 | 1 | 1 | H | O | $-O(i)C_3H_7$ | H | M.P. 85–86° C. |
| 28 | $CH_2$ | $CH_2$ | 1 | 1 | 0 | 1 | $C_2H_5O$ | O | $-O(i)C_3H_7$ | H | M.P. 144–146° C. |
| 29 | $CH_2$ | $CH_2$ | 0 | 1 | 1 | 1 | $(n)C_3H_7$ | O | $-O(i)C_3H_7$ | H | M.P. 90–92° C. |
| 30 | — | $CH_2$ | 1 | 0 | 0 | 1 | $CH_3OCH_2$ | O | $-O(i)C_3H_7$ | H | $n_D^{22.5}$ 1.5276 |
| 31 | — | $CH_2$ | 1 | 0 | 0 | 1 | $C_2H_5O$ | O | $-O(i)C_3H_7$ | H | M.P. 114–116° C. |
| 32 | — | $CH_2$ | 1 | 0 | 0 | 1 | $-\underset{\underset{O}{\parallel}}{C}-OCH_3$ | O | $-O(i)C_3H_7$ | H | M.P. 164.5–165.5° C. |
| 33 | $CH_2$ | $CH_2$ | 0 | 1 | 1 | 1 | Cl | O | $-O(i)C_3H_7$ | H | M.P. 126–128° C. |
| 34 | $-\underset{\underset{-CH-}{\mid}}{OCH_3}$ | $CH_2$ | 0 | 1 | 1 | 1 | $C_2H_5O$ | O | $-O(i)C_3H_7$ | H | M.P. 137–138.5° C. |
| 35 | $CH_2$ | $-\underset{\underset{-CH-}{\mid}}{OC_2H_5}$ | 0 | 1 | 1 | 1 | $C_2H_5O$ | O | $-O(i)C_3H_7$ | H | M.P. 124–126° C. |
| 36 | — | $CH_2$ | 1 | 0 | 0 | 1 | $CH_3OCH_2$ | S | $-OCH_3$ | H | M.P. 122–122.5° C. |
| 37 | $CH_2$ | $CH_2$ | 0 | 1 | 1 | 1 | $(n)C_3H_7$ | O | $-SC_2H_5$ | H | M.P. 89–90° C. |
| 38 | — | $CH_2$ | 1 | 0 | 0 | 1 | $-C{\equiv}N$ | O | $-O(i)C_3H_7$ | H | M.P. 115–118° C. |
| 39 | $CH_2$ | $CH_2CH_2$ | 0 | 1 | 0 | 0 | H | O | $-O(i)C_3H_7$ | H | M.P. 75–76° C. |
| 40 | $CH_2$ | $CH_2$ | 0 | 1 | 0 | 1 | H | O | $-O(i)C_3H_7$ | H | M.P. 102–103° C. |
| 41 | $CH_2$ | $CH_2$ | 0 | 1 | 1 | 1 | $C_2H_5O$ | O | $-OCH-CH_2OCH_3$ $\quad\mid$ $\quad CH_3$ | H | M.P. 91.5–94° C. |

In the practical usage of the compounds (I) as fungicides, they may be applied as such or in a formulation form such as dusts, wettable powders, oil sprays, emulsifiable concentrates, tablets, granules, fine granules, aerosols or flowables. Such formulation form can be formulated in a conventional manner by mixing at least one of the compounds (I) with an appropriate solid or liquid carrier(s) or diluent(s) and, if necessary, an appropriate adjuvant(s) (e.g. surfactants, adherents, dispersants, stabilizers) for improving the dispersibility and other properties of the active ingredient.

Examples of the solid carriers or diluents are botanical materials (e.g. flour, tobacco stalk powder, soybean powder, walnut-shell powder, vegetable powder, saw dust, bran, bark powder, cellulose powder, vegetable extract residue), fibrous materials (e.g. paper, corrugated cardboard, old rags), synthetic plastic powders, clays (e.g. kaolin, bentonite, fuller's earth), talcs, other inorganic materials (e.g. pyrophyllite, sericite, pumice, sulfur powder, active carbon) and chemical fertilizers (e.g. ammonium sulfate, ammonium phosphate, ammonium nitrate, urea, ammonium chloride).

Examples of the liquid carriers or diluents are water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methyl naphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, carbon tetrachloride), etc.

Examples of the surfactants are alkyl sulfuric esters, alkyl sulfonates, alkylaryl sulfonates, polyethylene glycol ethers, polyhydric alcohol esters, etc. Examples of the adherents and dispersants may include casein, gelatin, starch powder, carboxymethyl cellulose, gum arabic, alginic acid, lignin, bentonite, molasses, polyvinyl alcohol, pine oil and agar. As the stabilizers, there may be used PAP (isopropyl acid phosphate mixture), tricresyl phosphate (TCP), tolu oil, epoxydized oil, various surfactants, various fatty acids and their esters, etc.

The foregoing formulations generally contain at least one of the compounds (I) in a concentration of about 1 to 95% by weight, preferably of 2.0 to 80% by weight. By using the formulations, the compounds (I) are generally applied in such amounts as 2 to 100 g per 10 are.

When only the drug-resistant strains of phytopathogenic fungi are present, the compounds (I) may be used alone. However, when the drug-sensitive strains are present together with the drug-resistant strains, their alternate use with benzimidazole thiophanate fungicides and/or cyclic imide fungicides or their combined use with benzimidazole thiophanate fungicides and/or cyclic imide fungicides is favorable. In such alternate or combined use, each active ingredient may be employed as such or in conventional agricultural formulation forms. In case of the combined use, the weight proportion of the compound (I) and the benzimidazole thiophanate fungicide and/or the cyclic imide fungicide may be from about 1:0.1 to 1:10.0.

Typical examples of the benzimidazole thiophanate fungicides and the cyclic imide fungicides are shown in Table 2.

TABLE 2

| Compound | Structure | Name |
|---|---|---|
| A | benzimidazole with –NHCOOCH₃ and N-CONHC₄H₉(n) | Methyl 1-(butylcarbamoyl)benzimidazol-2-ylcarbamate |
| B | 2-(thiazolyl)benzimidazole | 2-(3-Thiazolyl)benzimidazole |
| C | benzimidazole-NHCOOCH₃ | Methyl benzimidazol-2-ylcarbamate |
| D | 2-(furyl)benzimidazole | 2-(2-Furyl)benzimidazole |
| E | benzene with two NHC(S)NHCOOCH₃ groups | 1,2-Bis(3-methoxycarbonyl-2-thioureido)benzene |
| F | benzene with two NHC(S)NHCOOC₂H₅ groups | 1,2-Bis(3-ethoxycarbonyl-2-thioureido)benzene |

TABLE 2-continued

| Compound | Structure | Name |
|---|---|---|
| G | [structure] | 2-(O,S—Dimethyl-phosphorylamino)-1-(3'-methoxycarbonyl-2'-thioureido)benzene |
| H | [structure] | 2-(O,O—Dimethylthio-phosphorylamino)-1-(3'-methoxycarbonyl-2'-thioureido)benzene |
| I | [structure] | N—(3',5'-Dichloro-phenyl)-1,2-dimethyl-cyclopropane-1,2-di-carboximide |
| J | [structure] | 3-(3',5'-Dichloro-phenyl)-1-isopropyl-carbamoylimida-zolidin-2,4-dione |
| K | [structure] | 3-(3',5'-Dichloro-phenyl)-5-methyl-5-vinyloxazolidin-2,4-dione |
| L | [structure] | Ethyl (RS)—3-(3',5'-dichlorophenyl)-5-methyl-2,4-dioxo-oxazolidine-5-carboxylate |

Besides, the compounds (I) may be also used in admixture with other fungicides, herbicides, insecticides, miticides, fertilizers, etc.

When the compounds (I) are used as fungicides, they may be applied in such amounts as 2 to 100 grams per 10 ares. However, this amount may vary depending upon formulation forms, application times, application methods, application sites, diseases, crops and so on, and therefore, they are not limited to said particular amounts.

Some practical embodiments of the fungicidal composition according to the invention are illustratively shown in the following Examples wherein % and part(s) are by weight.

FORMULATION EXAMPLE 1

Two parts of Compound No. 20, 88 parts of clay and 10 parts of talc are thoroughly pulverized and mixed together to obtain a dust formulation containing 2% of the active ingredient.

FORMULATION EXAMPLE 2

Thirty parts of Compound No. 29, 45 parts of diatomaceous earth, 20 parts of white carbon, 3 parts of sodium laurylsulfate as a wetting agent and 2 parts of calcium ligninsulfonate as a dispersing agent are mixed while being powdered to obtain a wettable powder formulation containing 30% of the active ingredient.

FORMULATION EXAMPLE 3

Fifty parts of Compound No. 30, 45 parts of diatomaceous earth, 2.5 parts of calcium alkylbenzenesulfonate as a wetting agent and 2.5 parts of calcium ligninsulfonate as a dispersing agent are mixed while being powdered to obtain a wettable powder formulation containing 50% of the active ingredient.

FORMULATION EXAMPLE 4

Ten parts of Compound No. 31, 80 parts of cyclohexanone and 10 parts of polyoxyethylene alkylaryl ether as an emulsifier are mixed together to obtain an emulsifiable concentrate formulation containing 10% of the active ingredient.

FORMULATION EXAMPLE 5

One part of Compound No. 5, 1 part of Compound I, 88 parts of clay and 10 parts of talc are thoroughly pulverized and mixed together to obtain a dust formulation containing 2 parts of the active ingredient.

FORMULATION EXAMPLE 6

Twenty parts of Compound No. 29, 10 parts of Compound J, 45 parts of diatomaceous earth, 20 parts of white carbon, 3 parts of sodium laurylsulfate as a wetting agent and 2 parts of calcium ligninsulfonate as a dispersing agent are mixed while being powdered to obtain a wettable powder composition containing 30% of the active ingredient.

FORMULATION EXAMPLE 7

Ten parts of Compound No. 30, 40 parts of Compound A, 45 parts of diatomaceous earth, 2.5 parts of calcium alkylbenzenesulfonate as a wetting agent and 2.5 parts of calcium ligninsulfonate as a dispersing agent are mixed while being powdered to obtain a wettable powder composition containing 50% of the active ingredient.

Typical test data indicating the excellent fungicidal activity of the compounds (I) are shown below. The compounds used for comparison are as follows:

| Compound | Remarks |
|---|---|
| Swep | Commercially available herbicide |
| Chlorpropham | Commercially available herbicide |
| Barban | Commercially available herbicide |
| CEPC | Commercially available herbicide |
| Propham | Commercially available herbicide |
| Chlorbufam | Commercially available herbicide |
| Benomyl | Commercially available fungicide |
| Thiophanate-methyl | Commercially available fungicide |
| Carbendazim | Commercially available fungicide |
| Thiabendazole | Commercially available fungicide |

EXPERIMENT 1

Protective activity test on powdery mildew of cucumber (*Sphaerotheca fuliginea*)

A flower pot of 90 ml volume was filled with sandy soil, and seeds of cucumber (var: Sagami-hanjiro) were sowed therein. Cultivation was carried out in a greenhouse for 8 days. Onto the resulting seedlings having cotyledons, the test compound formulated in an emulsifiable concentrate or wettable powder and diluted with water was sprayed at a rate of 10 ml per pot. Then, the seedlings were inoculated with a spore suspension of the drug-resistant or drug-sensitive strain of *Sphaerotheca fuliginea* by spraying and further cultivated in the greenhouse. Ten days thereafter, the infectious state of the plants was observed. The degree of damage was determined in the following manner, and the results are shown in Table 3.

The leaves examined were measured for a percentage of infected area and classified into the corresponding disease indices, 0, 0.5, 1, 2, 4:

| Disease index | Percentage of infected area |
|---|---|
| 0 | No infection |
| 0.5 | Infected area of less than 5% |
| 1 | Infected area of less than 20% |
| 2 | Infected area of less than 50% |

-continued

| Disease index | Percentage of infected area |
| --- | --- |
| 4 | Infected area of not less than 50% |

The disease severity was calculated according to the following equation:

Disease severity (%) =

$$\frac{\Sigma\{(\text{Disease index}) \times (\text{Number of leaves})\}}{4 \times (\text{Total number of leaves examined})} \times 100$$

The prevention value was calculated according to the following equation:

Prevention value (%) = 100 −

$$\frac{(\text{Disease severity in treated plot})}{(\text{Disease severity in untreated plot})} \times 100$$

TABLE 3

| Compound No. | Concentration of active ingredient (ppm) | Prevention value when inoculated with drug-resistant strain (%) | Prevention value when inoculated with drug-sensitive strain (%) |
| --- | --- | --- | --- |
| 1 | 500 | 100 | 0 |
| 5 | 500 | 100 | 0 |
| 9 | 200 | 100 | 0 |
| 25 | 200 | 100 | 0 |
| 26 | 200 | 100 | 0 |
| 29 | 200 | 100 | 0 |
| 30 | 500 | 100 | 0 |
| 31 | 200 | 100 | 0 |
| 33 | 500 | 100 | 0 |
| Swep | 200 | 0 | 0 |
| Chlorpropham | 200 | 0 | 0 |
| Barban | 200 | 25 | 0 |
| CEPC | 200 | 0 | 0 |
| Propham | 200 | 0 | 0 |
| Chlorbufam | 200 | 0 | 0 |
| Benomyl | 200 | 0 | 100 |
| Thiophanate-methyl | 200 | 0 | 100 |
| Carbendazim | 200 | 0 | 100 |

As understood from the results shown in Table 3, the compounds (I) of the invention show an excellent preventive effect on the drug-resistant strain but do not show any preventive effect on the tested drug-sensitive strain. To the contrary, commercially available known fungicides such as Benomyl, Thiophanate-methyl and Carbendazim show a notable controlling effect on the drug-sensitive strain but not on the drug-resistant strain. Other tested compounds structurally similar to the compounds (I) do not show any fungicidal activity on the drug-sensitive strain and the drug-resistant strain.

EXPERIMENT 2

Preventive effect on cercospora leaf spot of sugarbeet (*Cercospora beticola*)

A flower pot of 90 ml volume was filled with sandy soil, and seeds of sugarbeet (var: Detroit dark red) were sowed therein. Cultivation was carried out in a greenhouse for 20 days. Onto the resulting seedlings, the test compound formulation in an emulsifiable concentrate or wettable powder and diluted with water was sprayed at a rate of 10 ml per pot. Then, the seedlings were inoculated with a spore suspension of the drug-resistant or drug-sensitive strain of *Cercospora beticola* by spraying. The pot was covered with a polyvinyl chloride sheet to make a condition of high humidity, and cultivation was continued in the greenhouse for 10 days. The degree of damage was determined in the same manner as in Experiment 1, and the results are shown in Table 4.

TABLE 4

| Compound No. | Concentration of active ingredient (ppm) | Prevention value when inoculated with drug-resistant strain (%) | Prevention value when inoculated with drug-sensitive strain (%) |
| --- | --- | --- | --- |
| 5 | 500 | 100 | 0 |
| 6 | 500 | 100 | 0 |
| 8 | 500 | 100 | 0 |
| 9 | 500 | 100 | 0 |
| 20 | 500 | 100 | 0 |
| 25 | 500 | 100 | 0 |
| 29 | 500 | 100 | 0 |
| 30 | 500 | 100 | 0 |
| 31 | 500 | 100 | 0 |
| 33 | 500 | 100 | 0 |
| 41 | 500 | 100 | 0 |
| Swep | 200 | 0 | 0 |
| Chlorpropham | 200 | 0 | 0 |
| Barban | 200 | 34 | 0 |
| CEPC | 200 | 0 | 0 |
| Propham | 200 | 0 | 0 |
| Chlorbufam | 200 | 0 | 0 |
| Benomyl | 200 | 0 | 100 |
| Thiophanate-methyl | 200 | 0 | 100 |
| Carbendazim | 200 | 0 | 100 |

As understood from the results shown in Table 4, the compounds (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain. Other tested compounds structurally similar to the compounds (I) do not show any fungicidal activity on the drug-sensitive strain and the drug-resistant strain.

EXPERIMENT 3

Preventive effect on scab of pear (*Venturia nashicola*)

A plastic pot of 90 ml volume was filled with sandy soil, and seeds of pear (var: Chojuro) were sowed therein. Cultivation was carried out in a greenhouse for 20 days. Onto the resulting seedlings, the test compound formulated in an emulsifiable concentrate or wettable powder and diluted with water was sprayed at a rate of 10 ml per pot. Then, the seedlings were inoculated with a spore suspension of the drug-resistant or drug-sensitive strain of *Venturia nashicola* by spraying. The resulting plants were placed at 20° C. under a condition of high humidity for 3 days and then at 20° C. under irradiation with a fluorescent lamp for 20 days. The degree of damage was determined in the same manner as in Experiment 1, and the results are shown in Table 5.

TABLE 5

| Compound No. | Concentration of active ingredient (ppm) | Prevention value when inoculated with drug-resistant strain (%) | Prevention value when inoculated with drug-sensitive strain (%) |
| --- | --- | --- | --- |
| 5 | 500 | 100 | 0 |

TABLE 5-continued

| Compound No. | Concentration of active ingredient (ppm) | Prevention value when inoculated with drug-resistant strain (%) | Prevention value when inoculated with drug-sensitive strain (%) |
|---|---|---|---|
| 9 | 500 | 100 | 0 |
| 15 | 500 | 100 | 0 |
| 29 | 500 | 100 | 0 |
| 30 | 500 | 100 | 0 |
| 31 | 500 | 100 | 0 |
| 33 | 500 | 100 | 0 |
| Benomyl | 200 | 0 | 100 |
| Thiophanate-methyl | 200 | 0 | 100 |

As understood from the results shown in Table 5, the compounds (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

EXPERIMENT 4

Preventive effect on brown leaf-spot of peanut (*Cercospora arachidicola*)

Plastic pots of 90 ml volume was filled with sandy soil, and seeds of peanut (var: Chiba hanryusei) were sowed therein. Cultivation was carried out in a greenhouse for 14 days. Onto the resulting seedlings, the test compound formulated in an emulsifiable concentrate or wettable powder and diluted with water was sprayed at a rate of 10 ml per pot. Then, the seedlings were inoculated with a spore suspension of the drug-sensitive strain of *Cercospora arachidicola* by spraying. The resulting plants were covered with a polyvinyl chloride sheet to make a condition of humidity and cultivated in the greenhouse for 10 days. The degree of damage was determined in the same manner as in Experiment 1, and the results are shown in Table 6.

TABLE 6

| Compound No. | Concentration of active ingredient (ppm) | Prevention value when inoculated with drug-resistant strain (%) | Prevention value when inoculated with drug-sensitive strain (%) |
|---|---|---|---|
| 31 | 500 | 100 | 0 |
| Benomyl | 200 | 0 | 100 |
| Thiophanate-methyl | 200 | 0 | 100 |

As understood from the results shown in Table 6, the compounds (I) of the invention shown an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

EXPERIMENT 5

Preventive effect on gray mold of cucumber (*Botrytis cinerea*)

Plastic pots of 90 ml volume were filled with sandy soil, and seeds of cucumber (var: Sagami-hanjiro) were sowed therein. Cultivation was carried out in a greenhouse for 8 days to obtain cucumber seedlings expanding cotyledons. Onto the resulting seedlings, the test compound formulation in an emulsifiable concentrate or wettable powder and diluted with water was sprayed at a rate of 10 ml per pot. After air-drying, the seedlings were inoculated with mycelial disks (5 mm in diameter) of the drug-resistant or drug-sensitive strain of *Botrytis cinerea* by putting them on the leaf surfaces. After the plants were infected by incubating under high humidity at 20° C. for 3 days, the rates of disease severity were observed. The degree of damage was determined in the same manner as in Experiment 1, and the results are shown in Table 7.

TABLE 7

| Compound No. | Concentration of active ingredient (ppm) | Prevention value when inoculated with drug-resistant strain (%) | Prevention value when inoculated with drug-sensitive strain (%) |
|---|---|---|---|
| 1 | 500 | 100 | 0 |
| 2 | 500 | 100 | 0 |
| 3 | 500 | 100 | 0 |
| 4 | 500 | 100 | 0 |
| 5 | 200 | 100 | 0 |
| 6 | 500 | 100 | 0 |
| 7 | 500 | 100 | 0 |
| 8 | 500 | 100 | 0 |
| 9 | 200 | 100 | 0 |
| 10 | 500 | 100 | 0 |
| 11 | 500 | 100 | 0 |
| 12 | 500 | 100 | 0 |
| 13 | 500 | 100 | 0 |
| 14 | 500 | 100 | 0 |
| 15 | 500 | 100 | 0 |
| 16 | 500 | 100 | 0 |
| 17 | 500 | 100 | 0 |
| 18 | 500 | 100 | 0 |
| 19 | 500 | 100 | 0 |
| 20 | 500 | 100 | 0 |
| 21 | 500 | 100 | 0 |
| 22 | 500 | 100 | 0 |
| 23 | 500 | 100 | 0 |
| 24 | 500 | 100 | 0 |
| 25 | 500 | 100 | 0 |
| 26 | 500 | 100 | 0 |
| 27 | 500 | 100 | 0 |
| 28 | 500 | 100 | 0 |
| 29 | 500 | 100 | 0 |
| 30 | 500 | 100 | 0 |
| 31 | 500 | 100 | 0 |
| 32 | 500 | 100 | 0 |
| 33 | 500 | 100 | 0 |
| 34 | 500 | 100 | 0 |
| 35 | 500 | 100 | 0 |
| 36 | 500 | 100 | 0 |
| 37 | 500 | 100 | 0 |
| 38 | 500 | 100 | 0 |
| 39 | 500 | 100 | 0 |
| 40 | 500 | 100 | 0 |
| 41 | 500 | 100 | 0 |
| Benomyl | 200 | 0 | 100 |
| Thiophanate-methyl | 200 | 0 | 100 |

As understood from the results shown in Table 7, the compounds (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

EXPERIMENT 6

Preventive effect on gummy stem blight of cucumber (*Mycosphaerella melonis*)

Plastic pots of 90 ml volume were filled with sandy soil, and seeds of cucumber (var: Sagami-hanjiro) were sowed therein. Cultivation was carried out in a greenhouse for 8 days to obtain cucumber seedlings expanding cotyledons. Onto the resulting seedlings, the test compound formulated in an emulsifiable concentrate or wettable powder and diluted with water was sprayed at a rate of 10 ml per pot. After air-drying, the seedlings were inoculated with mycelial disks (5 mm in diameter) of the drug-resistant or drug-sensitive strain of *Mycosphaerella melonis* by putting them on the leaf surfaces. After the plants were infected by incubating under high humidity at 25° C. for 4 days, the rates of disease severity were observed. The degree of damage was determined in the same manner as in Experiment 1, and the results are shown in Table 8.

TABLE 8

| Compound No. | Concentration of active ingredient (ppm) | Prevention value when inoculated with drug-resistant strain (%) | Prevention value when inoculated with drug-sensitive strain (%) |
|---|---|---|---|
| 5 | 500 | 100 | 0 |
| 9 | 500 | 100 | 0 |
| 18 | 500 | 100 | 0 |
| 19 | 500 | 100 | 0 |
| 20 | 500 | 100 | 0 |
| 21 | 500 | 100 | 0 |
| 22 | 500 | 100 | 0 |
| 31 | 500 | 100 | 0 |
| 32 | 500 | 100 | 0 |
| Benomyl | 200 | 0 | 100 |
| Thiophanate-methyl | 200 | 0 | 100 |

As understood from the results shown in Table 8, the compounds (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

EXPERIMENT 7

Preventive effect on green mold of orange (*Penicillium italicum*)

Fruits of orange (var: Unshu) were washed with water and dried in the air. The fruits were immersed in a solution of the test compound prepared by diluting an emulsifiable concentrate comprising the test compound with water for 1 minute. After drying in the air, the fruits were inoculated with a spore suspension of the drug-resistant or drug-sensitive strain of *Penicillium italicum* by spraying and placed in a room of high humidity for 14 days. The degree of damage was determined in the following manner:

The fruits examined were measured for a percentage of infected area and classified into the corresponding indices, 0, 1, 2, 3, 4, 5:

| Disease index | Percentage of infected area |
|---|---|
| 0 | No infection |
| 1 | Infected area of less than 20% |
| 2 | Infected area of less than 40% |
| 3 | Infected area of less than 60% |
| 4 | Infected area of less than 80% |
| 5 | Infected area of not less than 80% |

Calculation of the degree of damage and the prevention value was made as in Experiment 1.
The results are shown in Table 9.

TABLE 9

| Compound No. | Concentration of active ingredient (ppm) | Prevention value when inoculated with drug-resistant strain (%) | Prevention value when inoculated with drug-sensitive strain (%) |
|---|---|---|---|
| 29 | 500 | 100 | 0 |
| Benomyl | 200 | 0 | 100 |
| Thiophanate-methyl | 200 | 0 | 100 |

As understood from the results shown in Table 9, the compounds (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

EXPERIMENT 8

Phytotoxicity on crop plants

Plastic pots of 150 ml volume were filled with sandy soil, and seeds of wheat (var: Norin No. 61), apple (var: Kogyoku) and peanut (var: Chiba hanryusei) were sowed therein. Cultivation was carried out in a greenhouse. Onto the resulting seedlings, the test compound formulated in an emulsifiable concentrate or wettable powder and diluted with water was sprayed. After cultivation in the greenhouse for an additional 10 days, the phytotoxicity was examined on the following criteria:

| Extent | Observation |
|---|---|
| − | No abnormality |
| + | Abnormality due to phytotoxicity observed in a part of crop plants |
| ++ | Abnormality due to phytotoxicity observed in entire crop plants |
| +++ | Crop plants withered due to phytotoxicity |

The results are shown in Table 10.

TABLE 10

| Compound No. | Concentration of active ingredient (ppm) | Phytotoxicity | | |
|---|---|---|---|---|
| | | Wheat | Apple | Peanut |
| 31 | 1000 | − | − | − |
| Barban | 1000 | − | ++ | ++ |
| CEPC | 1000 | − | ++ | ++ |
| Swep | 1000 | ++ | ++ | + |

As understood from the results shown in Table 10, the compounds of the formula (I) of the invention produce no material phytotoxicity, while commercially available herbicides having a chemical structure similar thereto produce considerable phytotoxicity.

EXPERIMENT 9

Preventive effect on powdery mildew of cucumber (*Sphaerotheca fuliginea*)

A plastic pot of 90 ml volume was filled with sandy soil, and seeds of cucumber (var: Sagami-hanjiro) were sowed therein. Cultivation was carried out in a greenhouse for 8 days. Onto the resulting seedlings having cotyledons, the test compound(s) formulated in an emulsifiable concentrate or wettable powder and diluted with water were sprayed at a rate of 10 ml per pot. Then, the seedlings were inoculated with a mixed spore suspension of the drug-resistant and drug-sensitive strain of *Sphaerotheca fuliginea* by spraying and further cultivated in the greenhouse. Ten days thereafter, the infectious state of the plants was observed. The degree of damage was determined in the same manner as in Experiment 1, and the results are shown in Table 11.

TABLE 11

| Compound No. | Concentration of active ingredient (ppm) | Prevention value (%) |
|---|---|---|
| 5 | 100 | 40 |
| 5 | 20 | 0 |
| 29 | 100 | 38 |
| 29 | 20 | 0 |
| 30 | 100 | 36 |
| 30 | 20 | 0 |
| 31 | 100 | 38 |
| 31 | 20 | 0 |
| 42 | 100 | 44 |
| 42 | 20 | 0 |
| A | 100 | 43 |
| A | 20 | 10 |
| B | 500 | 44 |
| B | 100 | 8 |
| C | 100 | 46 |
| C | 20 | 10 |
| D | 500 | 34 |
| D | 100 | 0 |
| E | 100 | 45 |
| E | 20 | 8 |
| F | 100 | 42 |
| F | 20 | 8 |
| G | 100 | 42 |
| G | 20 | 10 |
| H | 100 | 42 |
| H | 20 | 8 |
| 5 + A | 20 + 20 | 100 |
| 5 + F | 20 + 20 | 100 |
| 29 + A | 20 + 20 | 100 |
| 29 + B | 20 + 20 | 100 |
| 29 + C | 20 + 20 | 100 |
| 29 + D | 20 + 20 | 100 |
| 29 + G | 20 + 20 | 100 |
| 29 + H | 20 + 20 | 100 |
| 30 + A | 20 + 20 | 100 |
| 30 + B | 20 + 20 | 100 |
| 31 + E | 20 + 20 | 100 |
| 31 + F | 20 + 20 | 100 |
| 42 + A | 20 + 20 | 100 |
| 42 + E | 20 + 20 | 100 |

As understood from the results shown in Table 11, the combined use of the compounds (I) of the invention with benzimidazole thiophanate fungicides and/or cyclic imide fungicides show much more excellent preventive effect than their sole use.

EXPERIMENT 10

Preventive effect on gray mold of tomato (*Botrytis cinerea*)

A plastic pot of 90 ml volume was filled with sandy soil, and seeds of tomato (var: Fukuju No. 2) were sowed therein. Cultivation was carried out in a greenhouse for 4 weeks. Onto the resulting seedlings at the 4-leaf stage, the test compound(s) formulated in an emulsifiable concentrate or wettable powder and diluted with water were sprayed at a rate of 10 ml per pot. Then, the seedlings were inoculated with a mixed spore suspension of the drug-resistant and drug-sensitive strain of *Botrytis cinerea* by spraying and placed at 20° C. in a room of high humidity for 5 days. The degree of damage was determined in the same manner as in Experiment 1, and the results are shown in Table 12.

TABLE 12

| Compound No. | Concentration of active ingredient (ppm) | Prevention value (%) |
|---|---|---|
| 5 | 100 | 32 |
| 5 | 20 | 0 |
| 29 | 100 | 36 |
| 29 | 20 | 0 |
| 30 | 100 | 34 |
| 30 | 20 | 0 |
| 31 | 100 | 32 |
| 31 | 20 | 0 |
| I | 100 | 48 |
| I | 20 | 20 |
| J | 500 | 44 |
| J | 100 | 16 |
| K | 100 | 40 |
| K | 20 | 18 |
| L | 500 | 42 |
| L | 100 | 10 |
| 5 + I | 10 + 20 | 100 |
| 5 + J | 10 + 20 | 100 |
| 5 + K | 10 + 20 | 100 |
| 5 + L | 10 + 20 | 100 |
| 29 + I | 10 + 20 | 100 |
| 29 + K | 10 + 20 | 100 |
| 30 + I | 10 + 20 | 100 |
| 30 + L | 10 + 20 | 100 |
| 31 + I | 10 + 20 | 100 |
| 31 + J | 10 + 20 | 100 |

As understood from the results shown in Table 12, the combined use of the compounds (I) of the invention with benzimidazole or thiophanate fungicides and/or cyclic imide fungicides show much more excellent preventive effect than their sole use.

What is claimed is:

1. A compound of the formula:

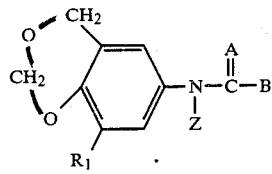

wherein $R_1$ is a lower alkyl group, a lower alkoxy group, a lower alkoxymethyl group, a lower alkoxycarbonyl group, a hydrogen atom, a halogen atom, or a cyano group; Z is a hydrogen atom, a lower alkyl group, a lower alkenyl group, a lower alkynyl group, a lower alkoxycarbonyl(lower)alkyl group or a group of the formula: —S—$R_3$ in which $R_3$ is a lower alkyl group, a phenyl group or a lower alkoxycarbonyl group; A is an oxygen atom or a sulfur atom; and B is a lower alkyl group, a lower alkenyl group, a cyclo(-lower)-alkyl group, a phenyl group or a group of the formula: —W—R₄ in which W is an oxygen atom or a sulfur atom and R₄ is a lower alkyl group, a lower alkenyl group, a lower alkynyl group, a halo(lower)alkenyl group, a halo(lower) alkynyl group, a cyclo(lower)alkyl group, a phenyl group optionally substituted with halogen or a lower alkyl group substituted with at least one member selected from the group consisting of halogen, cyano, phenyl, cyclo(lower)alkyl or lower alkoxy.

2. A fungicidal composition which comprises as an active ingredient a fungicidally effective amount of a compound of the formula:

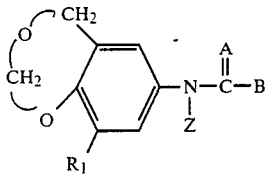

wherein R₁ is a lower alkyl group, a lower alkoxy group, a lower alkoxymethyl group, a lower alkoxycarbonyl group, a hydrogen atom, a halogen atom, or a cyano group; Z is a hydrogen atom, a lower alkyl group, a lower alkenyl group, a lower alkynyl group, a lower alkoxycarbonyl(lower)alkyl group or a group of the formula: —S—R₃ in which R₃ is a lower alkyl group, a phenyl group or a lower alkoxycarbonyl group; A is an oxygen atom or a sulfur atom; and B is a lower alkyl group, a lower alkenyl group, a cyclo(lower)alkyl group, a phenyl group or a group of the formula: —W—R₄ in which W is an oxygen atom or a sulfur atom and R₄ is a lower alkyl group, a lower alkenyl group, a lower alkynyl group, a halo(lower)alkenyl group, a halo(lower)alkynyl group, a cyclo(lower)alkyl group, a phenyl group optionally substituted with halogen or a lower alkyl group substituted with at least one member selected from the group consisting of halogen, cyano, phenyl, cyclo(lower)alkyl or lower alkoxy, and an inert carrier or diluent.

3. The fungicidal composition according to claim 2, which further comprises as additional active ingredient a benzimidazole or thiophanate fungicide and/or a cyclic imide fungicide.

4. The fungicidal composition according to claim 3, wherein the benzimidazole or thiophanate fungicide is methyl 1-(butylcarbamoyl)benzimidazol-2-ylcarbamate, 2-(2-furyl)benzimidazole, 2-(4-thiazolyl)benzimidazole, methyl benzimidazol-2-ylcarbamate, 1,2-bis(3-methoxycarbonyl-2-thioureido)benzene, 1,2-bis(3-ethoxycarbonyl-2-thioureido)benzene, 2-(O,S-dimethylphosphorylamino)-1-(3'-methoxycarbonyl-2'-thioureido)-benzene or 2-(O,O-dimethylthiophosphorylamino)-1-(3'-methoxycarbonyl-2'-thioureido)benzene and the cyclic imide fungicide is 3-(3',5'-dichlorophenyl)-1,2-dimethylcyclopropane-1,2-dicarboximide, 3-(3',5'-dichlorophenyl)-1-isopropylcarbamoylimidazolidine-2,4-dione, 3-(3',5'-dichlorophenyl)-5-methyl-5-vinyloxazoline-2,4-dione or ethyl (RS)-3-(3',5'-dichlorophenyl)-5-methyl-2,4-dioxooxazolidine-5-carboxylate.

5. A method for controlling plant pathogenic fungi which comprises applying a fungicidally effective amount of at least one compound according to claim 1, to plant pathogenic fungi.

6. The method according to claim 5, wherein the plant pathogenic fungi is a drug-resistant strain.

7. A method for controlling plant pathogenic fungi which comprises applying thereto a fungicidally effective amount of a mixture of a compound according to claim 1 and a benzimidazole or thiophanate fungicide and/or a cyclic imide fungicide.

8. The compound according to claim 1, wherein R₁ is lower alkoxy, Z is hydrogen, A is oxygen and B is lower alkoxy.

9. An aniline compound which is represented by the formula:

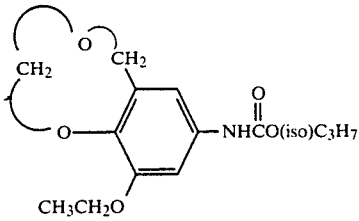

10. The composition according to claim 2, wherein R₁ is lower alkoxy, Z is hydrogen, A is oxygen and B is lower alkoxy.

11. A fungicidal composition which comprises as an essential active ingredient a fungicidally effective amount of the compound according to claim 9 and an inert carrier or diluent.

12. The composition according to claim 3, wherein R₁ is lower alkoxy, Z is hydrogen, A is oxygen and B is lower alkoxy.

13. The fungicidal composition according to claim 11 which further comprises as additional active ingredient a benzimidazole or thiophanate fungicide and/or a cyclic imide fungicide.

14. The method according to claim 5, wherein R₁ is lower alkoxy, Z is hydrogen, A is oxygen and B is lower alkoxy.

15. A method for controlling plant pathogenic fungi which comprises applying a fungicidally effective amount of the compound according to claim 9, to plant pathogenic fungi.

16. The method according to claim 7, wherein R₁ is lower alkoxy, Z is hydrogen, A is oxygen and B is lower alkoxy.

17. A method for controlling plant pathogenic fungi which comprises applying thereto a fungicidally effective amount of the compound according to claim 9, and a benzimidazole or thiophanate fungicide and/or a cyclic imide fungicide.

18. A compound of the formula:

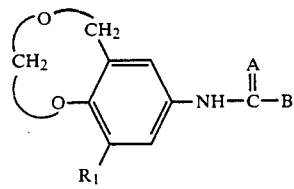

wherein R₁ is a lower alkyl group, a lower alkoxy group, a lower alkoxymethyl group, a lower alkoxycarbonyl group, a hydrogen atom, a halogen atom, or a cyano group; A is oxygen or sulfur; and B is a lower alkyl group, a lower alkenyl group, a cyclo(lower)-alkyl group, a phenyl group or a group of the formula:

—W—R$_4$ in which W is an oxygen atom or a sulfur atom and R$_4$ is a lower alkyl group, a lower alkenyl group, a lower alkynyl group, a halo(lower)alkenyl group, a halo(lower)alkynyl group, a cyclo(lower)alkyl group, a phenyl group optionally substituted with halogen or a lower alkyl group substituted with at least one member selected from the group consisting of halogen, cyano, phenyl, cyclo(lower)alkyl or lower alkoxy.

19. A fungicidal composition which comprises as an essential active ingredient a fungicidally effective amount of the compound according to claim 18 and an inert carrier or diluent.

20. The fungicidal composition according to claim 19, which further comprises as additional active ingredient a benzimidazole or thiophanate fungicide and/or a cyclic imide fungicide.

21. The fungicidal composition according to claim 20, the benzimidazole or thiophanate fungicide is methyl 1-(butylcarbamoyl)benzimidazol-2-ylcarbamate, 2-(2-furyl)benzimidazole, 2-(4-thiazolyl)benzimidazole, methyl benzimidazol-2-ylcarbamate, 1,2-bis(3-methoxycarbonyl-2-thio-ureido)benzene, 1,2-bis(3-ethoxycarbonyl-2-thioureido)benzene, 2-(O,S-dimethylphosphorylamino)-1-(3'-methoxycarbonyl-2'-thioureido)-benzene or 2-(O,O-dimethylthiophosphorylamino)-1-(3'-methoxycarbonyl-2'-thioureido)benzene and the cyclic imide fungicide is 3-(3',5'-dichlorophenyl)-1,2-dimethylcyclopropane-1,2-dicarboximide, 3-(3',5'-dichlorophenyl)-1-isopropylcarbamoylimidazolidine-2,4-dione, 3-(3',5'-dichlorophenyl)-5-methyl-5-vinyloxazoline-2,4-dione or ethyl (RS)-3-(3',5'-dichlorophenyl)-5-methyl-2,4-dioxo-oxazolidine-5-carboxylate.

22. A method for controlling plant pathogenic fungi which comprises applying a fungicidally effective amount of at least one of the compounds according to claim 25 to plant pathogenic fungi.

23. The method according to claim 22, wherein the plant pathogenic fungi is a drug-resistant strain.

24. A method for controlling plant pathogenic fungi which comprises applying thereto a fungicidally effective amount of a mixture of the compound according to claim 18 and a benzimidazole or thiophanate fungicide and/or a cyclic imide fungicide.

* * * * *